(12) United States Patent
Lebner et al.

(10) Patent No.: US 7,563,941 B2
(45) Date of Patent: Jul. 21, 2009

(54) MODULAR WOUND DRESSING SYSTEM

(75) Inventors: Michael Lebner, Wellesley Hills, MA (US); Raymond Barbuto, Dagsboro, DE (US)

(73) Assignee: Clozex Medical, LLC, Wellesley Hills, MA (US)

( * ) Notice: Subject to any disclaimer, the term of this patent is extended or adjusted under 35 U.S.C. 154(b) by 520 days.

(21) Appl. No.: 10/938,403

(22) Filed: Sep. 10, 2004

(65) Prior Publication Data
US 2006/0058721 A1 Mar. 16, 2006

(51) Int. Cl.
*A61F 13/00* (2006.01)
(52) U.S. Cl. .......................................................... 602/57
(58) Field of Classification Search ............. 602/41–59; 128/877, 889, 890
See application file for complete search history.

(56) References Cited

U.S. PATENT DOCUMENTS

| | | |
|---|---|---|
| 24,906 A | 7/1859 | Goodfellow |
| 1,074,413 A | 9/1913 | De Baun et al. |
| 1,230,444 A | 6/1917 | Teed |
| 1,969,188 A | 8/1934 | Spicer |
| 2,196,296 A | 5/1940 | Flynn |
| 2,532,011 A | 11/1950 | Dahlquist et al. |
| 2,762,371 A | 9/1956 | Guio |
| 2,818,865 A | 1/1958 | Jacoby, Jr. |
| RE24,906 E | 12/1960 | Ulrich |
| 3,020,186 A | 2/1962 | Lawrence |
| 3,329,548 A | 7/1967 | Blatz |
| 3,389,827 A | 6/1968 | Abere |
| 3,645,835 A | 2/1972 | Hodgson |
| 4,112,213 A | 9/1978 | Waldman |
| 4,141,363 A | 2/1979 | James et al. |
| 4,310,509 A | 1/1982 | Berglund et al. |
| 4,323,557 A | 4/1982 | Rosso et al. |

(Continued)

FOREIGN PATENT DOCUMENTS

GB 1299367 12/1972

(Continued)

OTHER PUBLICATIONS

Packaging and instruction sheet for "umbillical hernia plaster" produced by Lohmann GmbH & Co., KG (Postflach 23 43, D-56513 Neuwied, Germany); undated.

(Continued)

*Primary Examiner*—Michael A. Brown
(74) *Attorney, Agent, or Firm*—Pierce Atwood LLP; Kevin M. Farrell; Kathrine A. Wrobel

(57) ABSTRACT

Disclosed is a carrier-delivered dressing comprising a conformable film having first and second surfaces and a continuous outer perimeter. The conformable film includes a continuous strip of pressure-sensitive adhesive disposed on the first surface along a generally C-shaped first portion of the outer perimeter, and a second portion of the outer perimeter which is substantially adhesive-free. One or more release liners are provided which cover and protect the pressure-sensitive strip of adhesive prior to application. Alternative embodiments including a substantially continuous strip of pressure-sensitive adhesive around the continuous outer perimeter with one or more optionally removable release liners are also disclosed. Methods of use in which the dressings are applied in a shingled manner enable the convenient protection of long incisions or lacerations.

36 Claims, 3 Drawing Sheets

U.S. PATENT DOCUMENTS

| | | |
|---|---|---|
| 4,328,057 A | 5/1982 | Gutow |
| 4,374,520 A | 2/1983 | Grossmann |
| 4,413,621 A | 11/1983 | McCracken |
| 4,423,731 A | 1/1984 | Roomi |
| 4,472,480 A | 9/1984 | Olson |
| 4,485,809 A | 12/1984 | Dellas |
| 4,499,896 A | 2/1985 | Heinecke |
| RE31,887 E | 5/1985 | Hodgson |
| 4,524,095 A | 6/1985 | Gockel et al. |
| 4,545,371 A | 10/1985 | Grossmann |
| 4,549,063 A | 10/1985 | Ang |
| 4,587,146 A | 5/1986 | Anhauser |
| 4,590,022 A | 5/1986 | Cioca |
| 4,595,001 A | 6/1986 | Potter |
| 4,595,011 A | 6/1986 | Phillips |
| 4,596,738 A | 6/1986 | Metcalfe |
| 4,600,001 A | 7/1986 | Gilman |
| 4,614,183 A | 9/1986 | McCracken |
| 4,646,731 A | 3/1987 | Brower |
| 4,664,106 A | 5/1987 | Snedeker |
| 4,678,462 A * | 7/1987 | Vaillancourt ................ 604/180 |
| 4,706,662 A | 11/1987 | Thompson |
| 4,737,410 A | 4/1988 | Kantner |
| 4,753,232 A | 6/1988 | Ward |
| 4,787,380 A | 11/1988 | Scott |
| 4,825,866 A | 5/1989 | Pierce |
| 4,926,850 A | 5/1990 | Lott et al. |
| 4,950,282 A | 8/1990 | Beisang et al. |
| RE33,353 E | 9/1990 | Heinecke |
| RE33,727 E | 10/1991 | Sims |
| 5,088,483 A | 2/1992 | Heinecke |
| 5,106,383 A | 4/1992 | Mulder |
| 5,135,518 A | 8/1992 | Vera |
| 5,160,315 A | 11/1992 | Heinecke |
| 5,176,703 A | 1/1993 | Peterson |
| 5,263,970 A | 11/1993 | Preller |
| 5,336,162 A | 8/1994 | Ota |
| 5,425,702 A | 6/1995 | Carn et al. |
| 5,531,855 A | 7/1996 | Heinecke et al. |
| 5,534,010 A | 7/1996 | Peterson |
| 5,685,833 A | 11/1997 | Turngren |
| 5,733,251 A | 3/1998 | Johns |
| 5,733,570 A | 3/1998 | Chen |
| 5,738,642 A | 4/1998 | Heinecke et al. |
| 5,779,659 A | 7/1998 | Allen |
| 5,849,325 A | 12/1998 | Heinecke |
| 5,891,078 A | 4/1999 | Turngren |
| 5,979,450 A | 11/1999 | Baker et al. |
| 5,981,823 A | 11/1999 | Turngren |
| 6,129,971 A | 10/2000 | Brandt |
| 6,149,614 A | 11/2000 | Dunshee |
| 6,169,224 B1 * | 1/2001 | Heinecke et al. .............. 602/58 |
| 6,264,976 B1 | 7/2001 | Heinecke |
| 6,329,564 B1 | 12/2001 | Lebner |
| 6,364,188 B1 | 4/2002 | Dunshee |
| 6,420,622 B1 | 7/2002 | Johnston |
| 6,436,432 B2 | 8/2002 | Heinecke |
| 6,461,467 B2 | 10/2002 | Blatchford |
| 6,495,230 B1 | 12/2002 | Do Canto |
| 6,548,727 B1 | 4/2003 | Swenson |
| 6,566,575 B1 | 5/2003 | Stickels |
| 6,596,917 B2 | 7/2003 | Oyaski |
| 6,607,799 B1 | 8/2003 | Heinecke |
| 6,822,133 B2 | 11/2004 | Lebner |
| 6,831,205 B2 | 12/2004 | Lebner |
| 6,982,359 B1 | 1/2006 | Beaudry |
| 7,025,749 B2 * | 4/2006 | Propp ........................ 604/180 |
| 7,074,982 B2 * | 7/2006 | Knutson et al. ............... 602/42 |
| 2004/0106888 A1 | 6/2004 | Lutri et al. |
| 2004/0204740 A1 | 10/2004 | Weiser |
| 2005/0182443 A1 | 8/2005 | Jonn et al. |

FOREIGN PATENT DOCUMENTS

WO    WO/2005/079674 A1    9/2005

OTHER PUBLICATIONS

Stalar: "A more effective way to wound closure," by S. Paris, Abstract, Pub. by 43 Intern'l Sci. and Eng. Fair, Nashville, Tennessee, May 10, 1992, p. 257.

Paris, Stacy: "Is there a more effective way to accomplish wound closure than those presently employed?"; author indicates abstract published by South Carolina Junior Academy of Science, Feb. 1991; applicants have not independently verified this publication date.

* cited by examiner

MODULAR WOUND DRESSING SYSTEM

BACKGROUND OF THE INVENTION

Incisions, lacerations or other wounds requiring dressings can vary greatly in length. Such wounds are preferably covered by a waterproof, vapor-permeable membrane to promote the healing process. Although a wide range of conformable film dressings are known in the art, currently there exists no wound dressing which is readily adaptable for use in connection with wounds having varying lengths which are free of adhesive on or in the wound area.

SUMMARY OF THE INVENTION

The present invention relates in one aspect to a carrier-delivered dressing comprising a conformable film having first and second surfaces and a continuous outer perimeter. The conformable film includes a continuous strip of pressure-sensitive adhesive disposed on the first surface only along a generally C-shaped first portion of the outer perimeter, and includes a second portion of the outer perimeter which is substantially adhesive-free. One or more release liners are provided which cover and protect the pressure-sensitive strip of adhesive prior to application. Also provided is a carrier releasably attached to at least a portion of the second surface of the conformable film which facilitates the handling and application of the conformable film.

In another embodiment, the invention relates to a carrier-delivered dressing which includes a conformable film having first and second surfaces and a continuous outer perimeter. In this embodiment, the continuous outer perimeter includes a continuous strip of pressure-sensitive adhesive. This continuous strip comprises two sections, a generally C-shaped section and a second section. One or more release liners cover the pressure-sensitive strip of adhesive on the generally C-shaped section. An optionally removable release liner protects the second section. A carrier substrate is releasably attached to at least a portion of the second surface of the conformable film to facilitate application.

In preferred embodiments of the invention, the conformable film is clear and/or breathable. It is also preferable that the carrier be produced from a clear substrate to enable visualization of the surface to which the conformable film is to be applied during the application process. As an alternative to a clear carrier substrate, a cut defining a window may be introduced into the carrier substrate. The area of the carrier remaining between the cut defining a window and the outer perimeter of the carrier substrate defines a window frame. During the application process the surface to which the conformable film is to be applied can be visualized through the window.

In use, one or more dressings of the present invention may be used to form a protected or partially protected zone around a wound (e.g., a laceration or incision) with no adhesive on or touching the wound. The use of a plurality of the dressings of the present invention, applied in a shingled manner, may be used to extend a partially protected zone which, when the desired length is reached, may be sealed (e.g., with a tape strip or adhesive composite) to form a fully protected zone.

DETAILED DESCRIPTION OF THE INVENTION

Figure 1:
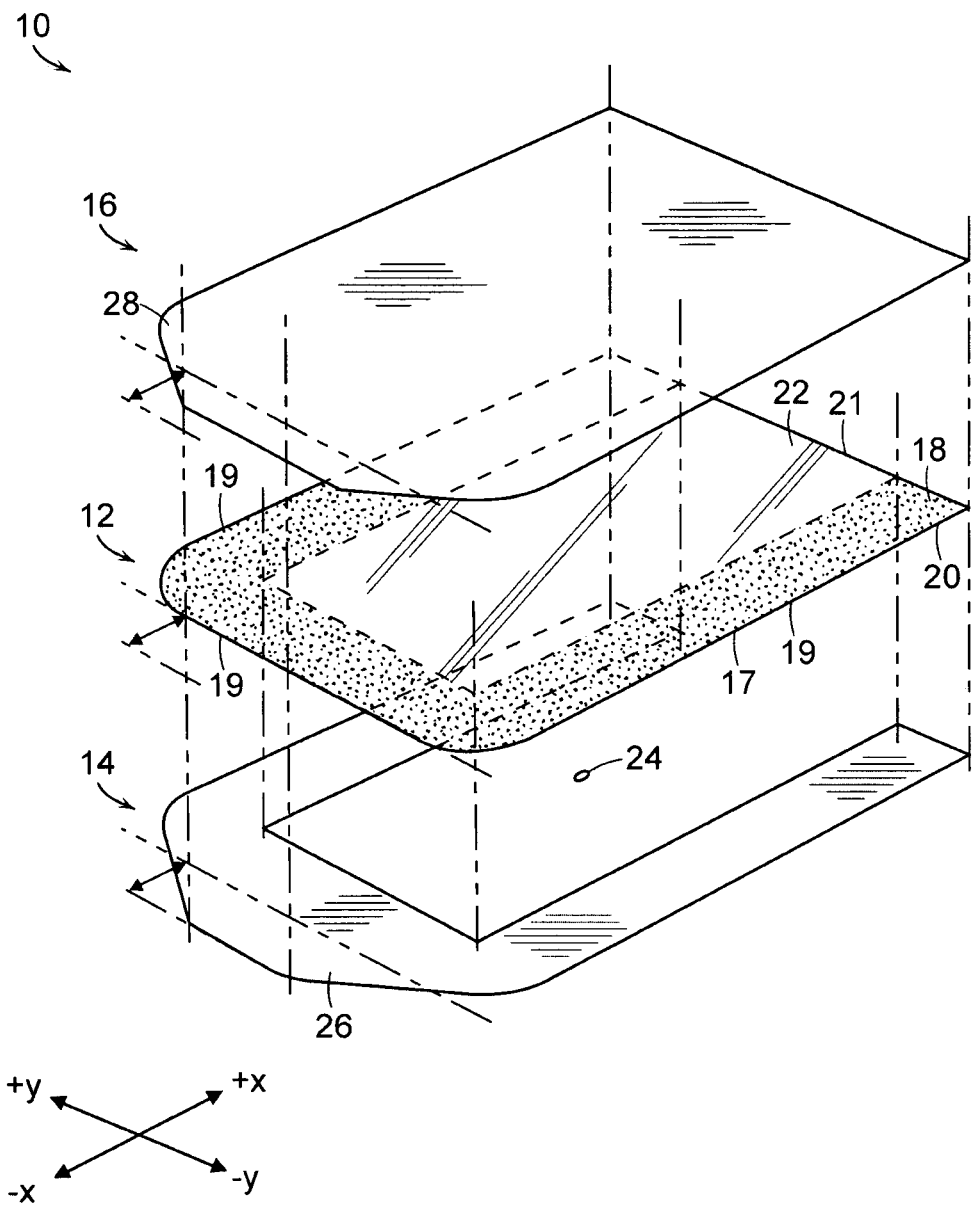
FIG. 1 is an exploded perspective view of a wound dressing of the present invention with a continuous strip pressure-sensitive adhesive applied along a generally C-shaped portion of the perimeter of a conformable film.

The present invention relates to a carrier-delivered dressing where no adhesive directly touches the wound and which is particularly well-suited for the dressing of lacerations or incisions of variable length. As discussed in the Background of the Invention section, a wide range of conformable dressings, many of which are carrier-delivered, are known in the art. Conformable, breathable wound dressing films are extremely thin, and this is responsible, in large part, for the comfort of these dressings. A carrier is required to enable the easy application of such thin films without introducing wrinkles or folds in the film.

Embodiments of the present invention are particularly well-suited for use in connection with long incisions or lacerations due to the fact that one end of the device is designed so that it can cross over a portion of the laceration or incision without contacting the laceration or incision with adhesive. In one embodiment, the present invention relates to a carrier-delivered dressing comprising a conformable film having at least a portion of a surface coated with a pressure-sensitive adhesive (sometimes referred to as a film/adhesive composite). Preferably, the conformable film is a polymeric film. Such polymeric films include, for example, elastomeric polyurethane, polyester or polyether block amide films.

Other desirable attributes of the film include a translucent or clear property. It is also preferable that the film has the ability to exclude water, dirt or bacteria from the laceration or incision, while permitting the transfer of water vapor from the covered site. A preferred property of the film/adhesive composite is that it has the ability to transmit water vapor at a rate similar to or greater than human skin. Values for such water vapor transfer are known in the art and reported, for example, in U.S. Pat. No. 5,738,642 the disclosure of which is incorporated herein by reference.

A variety of pressure-sensitive adhesives are known in the art which are suitable for the attachment of a polymer film to human skin without stimulating an allergic response, such materials are referred to as "hypoallergenic". Such adhesives are described, for example, in U.S. Pat. Nos. Re. 24,906, 3,389,827, 4,112,213, 4,310,509, and 4,323,557, the disclosures of which are incorporated herein by reference. As will be understood from the description which follows, large portions of the film dressing of the present invention are free of pressure-sensitive adhesive, thereby rendering the vapor permeability characteristics of the applied pressure-sensitive adhesive less important than would be the case if an entire surface of the film were coated.

Those skilled in the art will recognize that release liners suitable for use in protecting the pressure-sensitive adhesive coatings can be produced from a wide range of materials. Such materials include, for example, kraft paper, polyethylene, polypropylene, polyester or composites of these materials. The liners are preferably coated with release agents including, for example, fluorochemicals or silicones.

The substrate used to produce the carrier element of the carrier-delivered dressing of the present invention is substantially more rigid than the conformable film which it is used to deliver. This more rigid substrate enables application of the conformable film dressing with minimal wrinkling and folding of the conformable film. Absent a carrier element of the type described herein, application of a thin conformable film of the type used in connection with the present invention would be extremely difficult and impractical.

In preferred embodiments, the carrier is heat-sealable to the conformable film. A low-adhesion coating on the conformable film may optionally be used on the surface attached to the carrier. The low adhesion coating is discussed in greater detail below. Preferred carrier substrates include, for example, polyethylene/vinyl acetate copolymer-coated papers, polyester films, and high-density polyethylene or other polymeric composites. A clear carrier is preferred to enable visualization during application. Printed, translucent, or colored carrier substrates are also suitable. Non-clear carrier substrates may be modified to include a cut defining a window to enable visualization through the window of an application surface during the application process. The introduction of such a cut defining a window is known in the art and disclosed, for example, in U.S. Pat. Nos. 5,738,642 and 5,531,855. The window frame remaining following introduction of the cut defining a window is represented by the area of the carrier between the cut defining the window and the outer perimeter or outer edge of the carrier substrate. Cuts may be provided in the carrier substrate to facilitate removal of the carrier following application of the conformable film to the skin. This is particularly important in embodiments including a cut defining a window in the carrier substrate. In such embodiments, an additional cut connecting the cut defining the window to a portion of the outer edge of the substrate facilitates removal of the carrier following application of the conformable film.

The use of a low-adhesion coating on the surface of the conformable backing which is attached to the carrier element is preferred. A suitable low-adhesion coating comprising a solution of polyvinyl N-octadecyl carbamate and a blend of silicone resins is described in U.S. Pat. No. 5,738,642, the disclosure of which is incorporated herein by reference. Such a low-adhesion coating is compatible with the heat seal bond between the carrier and the conformable film, and the low-adhesion property is retained after heat-sealing.

As previously discussed, embodiments of the present invention are particularly well-suited for use in connection with long incisions or lacerations due to the fact that one end of the device is designed so that it bridges a portion of the laceration or incision without exposing the laceration or incision to adhesive. Use of the disclosed dressing in connection with wounds other than incisions or lacerations is intended to be encompassed within the scope of the present invention. Preferred embodiments of the present invention are discussed in detail in the following section.

PREFERRED EMBODIMENTS

Referring to FIG. 1, a preferred embodiment of the present invention is depicted diagrammatically. The carrier-delivered dressing 10 is comprised of 3 layers of substrate material: a conformable film 12, a release liner 14 and carrier material 16. Conformable film 12, has an upper surface 18 and a lower surface (not shown) and a continuous outer perimeter 17. A continuous strip of pressure-sensitive adhesive 20 is provided on a portion of the lower surface along a continuous generally C-shaped first portion 19 of the outer perimeter and is shown in phantom in FIG. 1. A second portion 21 of the outer perimeter of the lower surface is adhesive-free. The portion of the outer perimeter of the lower surface of the conformable film which contains a border of pressure-sensitive adhesive 20 defines a partially protected zone 22. By definition, the partially protected zone has a strip of pressure-sensitive adhesive which defines its boundary in the +y, −y and −x dimensions, relative to a central point 24 in the partially protected zone. As described below in connection with the description of FIG. 2, the partially protected zone is preferably sealed to form a fully protected zone in the final step of the wound dressing process (i.e., through the application of a tape strip or other adhesive composite or through the removal of an optionally removable release liner, depending upon the embodiment being used). The adhesive on the generally C-shaped first portion 19 incompletely surrounds the wound upon application of a single device. There are no strict requirements as to the size or specific shape of the first portion 19, but only that it be generally C-shaped. The generally C-shaped first portion 19 may be comprised of linear or curved elements in the perimeter.

The conformable film may comprise a first, second, third, and fourth edge, wherein the strip of pressure-sensitive adhesive 20 is disposed on a first surface along each one of said first, second, and third edges, with the fourth edge being substantially free of pressure-sensitive adhesive except for adhesive portions which continue from the edges adjacent to the fourth edge. In this embodiment, one or more release liners covers said pressure-sensitive adhesive along said first, second, and third edges.

Prior to use, the pressure-sensitive adhesive boundary 20 is protected with one or more release liners 14. Release liner 14 optionally includes a tab 26 which extends beyond the conformable film backing 12 in the assembled carrier-delivered dressing, thereby facilitating removal of the release liner prior to contacting the pressure-sensitive adhesive of the conformable film to the skin of an individual.

The second surface of the conformable backing 18 is releasably attached to carrier sheet 16. The bond between the upper surface 18 of conformable backing 12, and the lower surface (not shown in FIG. 1) of carrier sheet 16 is weaker than the bond between the pressure-sensitive adhesive 20 and the skin of the individual to whom the conformable film is applied. Thus, the carrier sheet 16 is used to deliver the conformable film to the skin following removal of one or more release liners 14. When the conformable film has been applied to the skin, the relatively weak bonding between the carrier sheet and the conformable film is broken by peeling the carrier 16 away from the skin and leaving the conformable film 12 in place on the skin. The carrier sheet 16 is discarded following removal. As discussed above, a heat seal bond provides a suitably weak connection between the upper surface 18 of the conformable film 12, and the carrier 16. An optional low-adhesion coating on the upper surface 18 of the conformable film 12 contributes to a suitably weak bond. The use of a clear carrier enables a user to apply the conformable film with precision. Tab 28 is provided on carrier sheet 16 to enable one to readily initiate separation of the carrier from the applied conformable film 12. One of skill in the art will recognize that the number and positions of such tabs is a matter of design choice.

Figure 2:
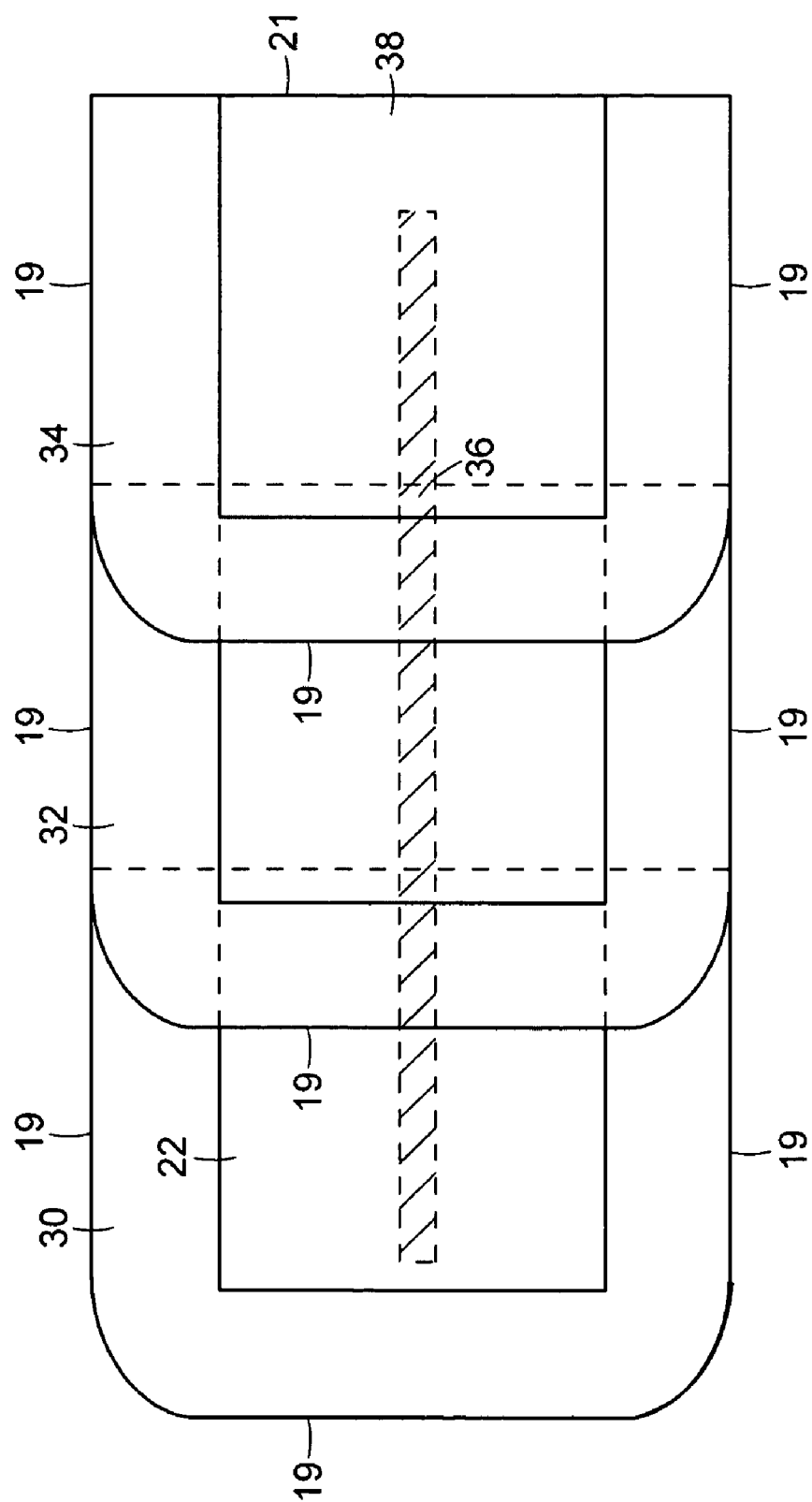
FIG. 2 is a top view representing three wound dressings of the present invention applied in a shingled manner to protect an incision.

Referring to FIG. 2, three dressings of the present invention are shown applied over a long incision 36. Dressings 30, 32 and 34 are applied in sequence with the substantially adhesive-free end bridging the incision or laceration and protecting it from adhesive on the overlapped and shingled adjacent dressing. As shown in FIG. 2, the portion of conformable films 30, 32 and 34 which contain pressure-sensitive adhesive 20 does not make contact with incision 36. Essentially, the addition of conformable films 32 and 34 effects the extension of the partially protected zone 22 initially established with the application of conformable film 30. The open end 38 of partially protected zone 22 is preferably closed or sealed following extension beyond the incision or laceration using, for example, a wide tape strip or other adhesive/film composite thereby forming a fully protected zone.

One of skill in the art will recognize that carrier-delivered dressings similar to that shown in FIG. 1, but containing a pressure-sensitive adhesive border around the entire continuous perimeter, can be modified to perform in a manner substantially similar to the dressing shown in FIG. 1. This can be accomplished, for example, by masking a portion of the pressure-sensitive adhesive using a separately removable release liner. Alternatively, a dressing having a removable film/adhesive portion could be designed to facilitate convenient and sterile removal of a pressure-sensitive adhesive-backed portion of film, thereby enabling similar sequential application of dressings to provide an extended protected zone.

The carrier-delivered dressing comprising a conformable film having a continuous strip of pressure-sensitive adhesive along a continuous outer perimeter comprises two sections: a generally C-shaped section 19; and a second section 21. This carrier-delivered dressing further comprises one or more release liners covering the pressure-sensitive strip of adhesive on the generally C-shaped section 19; an optionally removable release liner protecting the second section 21; and a carrier releasably attached to at least a portion of the second surface of the conformable film. Alternatively, a carrier-delivered dressing of the present invention may comprise a conformable film having a strip of pressure-sensitive adhesive disposed on said first surface along each one of said first, second, third and fourth edges; one or more release liners covering said pressure-sensitive adhesive along said first, second and third edges; and an optionally removable release liner covering the pressure-sensitive adhesive disposed along at least a portion of the fourth edge. In this embodiment, the optionally removable release liner is removable independently of other release liners associated with the carrier-delivered dressing.

Figure 3:
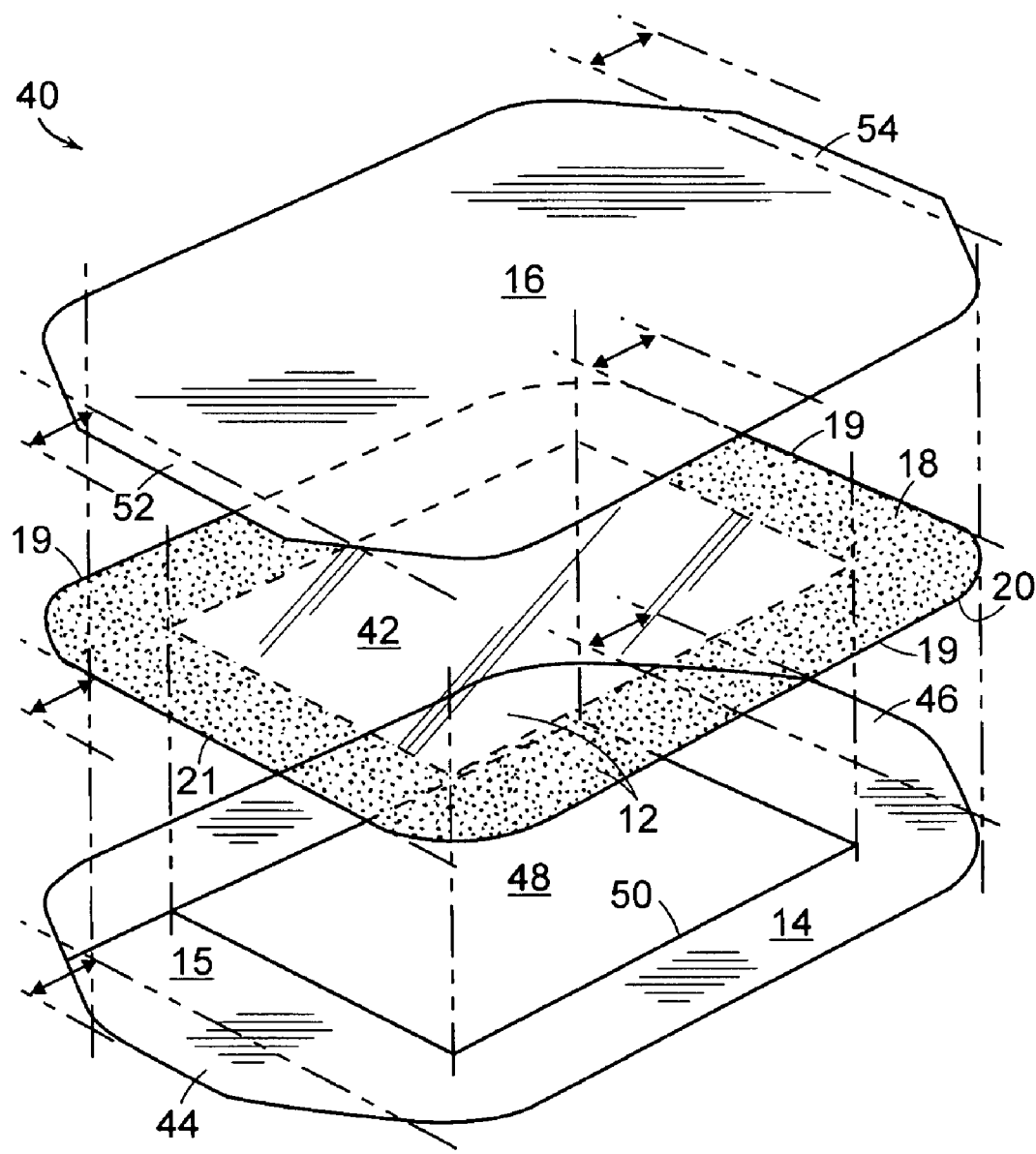
FIG. 3 is an exploded perspective view of a wound dressing of the present invention with a continuous strip of pressure-sensitive adhesive applied along the entire outer perimeter of a conformable film with two or more release liners, at least one of which is optionally removable.

Referring to FIG. 3, such an embodiment of the present invention is depicted diagrammatically. The carrier-delivered dressing 40 is comprised of 3 layers of substrate material: a conformable film 12, a release liner 14 and carrier material 16. Conformable film 12, has a border of pressure-sensitive adhesive 20 on a first surface (the lower surface) which surrounds an adhesive-free zone 42. Prior to use, the pressure-sensitive adhesive is protected by release liners 14 and 15. Release liners 14 and 15 include tabs 44 and 46 which extend beyond the point of contact with pressure-sensitive adhesive 20, thereby facilitating removal of the release liners, if desirable, prior to application of the conformable film to the skin. Clearly the removal of at least one of the release liners 14, is required prior to application of the conformable backing to the skin. However, embodiments of the present invention are intended for use in dressing long lacerations or incisions. Thus, by removing only one release liner 14, the dressing of the present invention can be used in an overlapping or shingled format to dress a long incision or laceration without adhesive contact to the injured area. When used in this way, release liner 15 prevents contact between a portion of the pressure-sensitive adhesive border and the injured area to be dressed. The release liner 14 is shown with a window 48 cut from the central portion. The frame of this window 50 corresponds generally to the inner boundary of the pressure-sensitive adhesive border on the conformable film of the assembled carrier-delivered dressing. The positioning and nature of the adhesive is such that when multiple devices are applied in tandem to a wound or incision, the adhesive functions to form a protective seal, preventing contamination of the wound from a non-sterile environment.

The second surface of the conformable backing 12 (the upper surface as shown in FIG. 1) is attached to lower surface of a carrier sheet 16. The bond between the conformable backing 12, and the carrier sheet 16 is weaker than the bond between the pressure-sensitive 20 and the skin of the individual to whom the conformable film is applied. Thus, the carrier sheet 16 is used to deliver the conformable film to the skin following removal of one or more release liners 14 and 15. When the conformable film has been applied to the skin, the relatively weak bonding between the carrier sheet and the conformable film is broken as the carrier sheet is removed and discarded. As discussed above, a heat seal bond provides a suitably weak connection between the conformable film and the carrier. An optional low-adhesion coating on the upper surface of the conformable film contributes to a suitably weak bond. The use of a clear carrier enables a user to apply the conformable film with precision. Tabs 52 and 54 are provided on carrier sheet 16 to enable one to readily initiate separation of the carrier from the applied conformable film 12.

The serial application of the dressings of this embodiment, without the removal of release liner 15, effects the extension of the protected zone as described above in connection with the embodiment lacking pressure-sensitive adhesive along a portion of the outer perimeter. When the final dressing is applied after the protected zone has been sufficiently extended, release liner 15 can be removed, thereby effectively sealing the protected zone.

Embodiments of the present invention can be provided in a roll format with the adhesive-free "open end" or the optionally removable release liner being located at the center of the roll. When provided with a rolled dressing as described herein, a user would unroll a portion of the dressing, remove a portion of the release liner and begin the application process by forming a partially protected zone around one end of the wound. This process would continue until the roll was exhausted, or until the applied portion extended beyond the area to be protected. If the roll were exhausted before the area to be protected was fully covered by the conformable film, a second dressing of the present invention (in roll or non-roll form) would be used to extend the partially protected zone (after first removing the carrier sheet from the first-applied dressing). Excess portions of the dressing extending beyond the desired coverage area could be removed by cutting off the unwanted excess. The partially protected zone in which the area to be protected is fully covered, but unsealed at one end, is then sealed rendered fully protected by the application of a tape strip or other adhesive composite.

The invention claimed is:

1. A carrier-delivered dressing comprising:
   a) a conformable film having first and second surfaces and a continuous outer perimeter;
   b) a continuous strip of pressure-sensitive adhesive disposed on said first surface along a generally C-shaped first portion of the outer perimeter, a second portion of the outer perimeter being adhesive-free;
   c) one or more release liners covering said pressure-sensitive strip of adhesive; and
   d) a carrier releasably attached to at least a portion of the second surface of the conformable film.

2. The carrier-delivered dressing of claim 1 wherein the conformable film is clear.

3. The carrier-delivered dressing of claim 1 wherein the conformable film is breathable.

4. The carrier-delivered dressing of claim 1 wherein the carrier is clear.

5. The carrier-delivered dressing of claim 1 wherein the carrier includes a cut defining a window enabling visualization through the window of an application surface during the application process.

6. The carrier-delivered dressing of claim 1 further comprising a low-adhesion coating on at least a portion of the second surface of the conformable film.

7. The carrier-delivered dressing of claim 1 wherein the device is packaged in a roll form with the central axis of the roll corresponding to a portion of the conformable film which is adhesive-free.

8. A carrier-delivered dressing comprising:
  a) a conformable film having first and second surfaces and a continuous outer perimeter, the continuous outer perimeter having a continuous strip of pressure-sensitive adhesive comprising two sections:
    i) a generally C-shaped section; and
    ii) a second section;
  b) one or more release liners covering the pressure-sensitive strip of adhesive on the generally C-shaped section;
  c) an optionally removable release liner protecting the second section; and
  d) a carrier releasably attached to at least a portion of the second surface of the conformable film.

9. The carrier-delivered dressing of claim 8 wherein the conformable film is clear.

10. The carrier-delivered dressing of claim 8 wherein the conformable film is breathable.

11. The carrier-delivered dressing of claim 8 wherein the carrier is clear.

12. The carrier-delivered dressing of claim 8 wherein the carrier includes a cut defining a window, enabling visualization through the window of an application surface during the application process.

13. The carrier-delivered dressing of claim 8 further comprising a low-adhesion coating on at least a portion of the second surface of the conformable film.

14. The carrier-delivered dressing of claim 8 wherein the device is packaged in a roll form with the central axis of the roll corresponding a portion of the conformable film containing the second section of pressure sensitive adhesive.

15. A carrier-delivered dressing comprising:
  a) a conformable film having first and second surfaces and first, second, third and fourth edges;
  b) a strip of pressure-sensitive adhesive disposed on said first surface along each one of said first, second, and third edges, the fourth edge being pressure-sensitive adhesive-free;
  c) one or more release liners covering said pressure-sensitive adhesive along said first, second and third edges; and
  d) a carrier releasably attached to at least a portion of the second surface of the conformable film.

16. The carrier-delivered dressing of claim 15 wherein the conformable film has a major and a minor axis and the fourth edge is oriented in a direction generally parallel with the minor axis.

17. The carrier-delivered dressing of claim 15 wherein the conformable film is clear.

18. The carrier-delivered dressing of claim 15 wherein the conformable film is breathable.

19. The carrier-delivered dressing of claim 15 wherein the carrier is clear.

20. The carrier-delivered dressing of claim 15 wherein the carrier includes a cut defining a window, enabling visualization through the window of an application surface during the application process.

21. The carrier-delivered dressing of claim 15 further comprising a low-adhesion coating on at least a portion of the second surface of the conformable film.

22. The carrier-delivered dressing of claim 15 wherein the device is packaged in roll form with the central axis of the roll corresponding approximately to the fourth edge of the conformable film.

23. A method for dressing a wound or incision, comprising:
  a) providing one or more wound dressings comprising:
    i) a conformable film having first and second surfaces and a continuous outer perimeter;
    ii) a continuous strip of pressure-sensitive adhesive disposed on said first surface along a generally C-shaped first portion of the outer perimeter, a second portion of the outer perimeter being adhesive-free;
    iii) one or more release liners covering said pressure-sensitive strip of adhesive; and
    iv) a carrier releasably attached to at least a portion of the second surface of the conformable film;
  b) applying a first wound dressing to the skin of an individual such that the continuous strip of pressure-sensitive adhesive seals a protected zone around a first end of the wound or incision;
  c) optionally applying additional wound dressings in a shingled manner to extend the protected zone along the full length of the wound or incision while avoiding contact between the pressure-sensitive adhesive and the wound or incision; and
  d) sealing the protected zone following extension of the protected zone beyond the second end of the wound or incision.

24. The method of claim 23 wherein the conformable film is clear.

25. The carrier-delivered dressing of claim 23 wherein the conformable film is breathable.

26. The method of claim 23 wherein the carrier is clear.

27. The carrier-delivered dressing of claim 23 wherein the carrier includes a cut defining a window enabling visualization through the window of an application surface during the application process.

28. The method of claim 23 further comprising a low-adhesion coating on at least a portion of the second surface of the conformable film.

29. The method of claim 23 wherein the device is packaged in a roll form with the central axis of the roll corresponding to a portion of the conformable film which is adhesive-free.

30. A method for dressing a wound or incision, comprising:
  a) providing one or more wound dressings comprising:
    i) a conformable film having first and second surfaces and a continuous outer perimeter, the continuous outer perimeter having a continuous strip of pressure-sensitive adhesive comprising two sections:
      (1) a generally C-shaped section; and
      (2) a second section;
    ii) one or more release liners covering the pressure-sensitive strip of adhesive on the generally C-shaped section;
    iii) an optionally removable release liner protecting the second section; and
    iv) a carrier releasably attached to at least a portion of the second surface of the conformable film;
  b) applying a first wound dressing to the skin of an individual such that the generally C-shaped section of pressure-sensitive adhesive seals a protected zone around a first end of the wound or incision;

c) optionally applying additional wound dressings in a shingled manner to extend the protected zone along the full length of the wound or incision while avoiding contact between the pressure-sensitive adhesive and the wound or incision; and d) sealing the protected zone following extension of the protected zone beyond the second end of the wound or incision.

31. The method of claim 30 wherein the conformable film is clear.

32. The method of claim 30 wherein the conformable film is breathable.

33. The method of claim 30 wherein the carrier is clear.

34. The method of claim 30 wherein the carrier includes a cut defining a window, enabling visualization through the window of an application surface during the application process.

35. The method of claim 30 further comprising a low-adhesion coating on at least a portion of the second surface of the conformable film.

36. The method of claim 30 wherein the device is packaged in a roll form with the central axis of the roll corresponding a portion of the conformable film containing the second section of pressure sensitive adhesive.

* * * * *